(12) United States Patent
Schulze-Forster et al.

(10) Patent No.: US 8,110,374 B2
(45) Date of Patent: Feb. 7, 2012

(54) METHOD FOR PREDICTING THE RISK OF TRANSPLANT REJECTION AND IMMUNOLOGICAL TESTKIT

(75) Inventors: Kai Schulze-Forster, Teltow (DE); Harald Heidecke, Berlin (DE)

(73) Assignee: Cell Trend GmbH, Luckenwalde (DE)

( * ) Notice: Subject to any disclaimer, the term of this patent is extended or adjusted under 35 U.S.C. 154(b) by 742 days.

(21) Appl. No.: 10/477,223

(22) PCT Filed: May 13, 2002

(86) PCT No.: PCT/EP02/05251
§ 371 (c)(1),
(2), (4) Date: May 24, 2004

(87) PCT Pub. No.: WO02/093171
PCT Pub. Date: Nov. 21, 2002

(65) Prior Publication Data
US 2004/0192634 A1  Sep. 30, 2004

(30) Foreign Application Priority Data
May 11, 2001 (DE) .................. 101 23 929

(51) Int. Cl.
*G01N 33/53* (2006.01)
*G01N 33/543* (2006.01)
*G01N 33/564* (2006.01)

(52) U.S. Cl. ....... 435/7.92; 422/425; 435/7.1; 435/7.21; 435/7.93; 435/7.95; 435/975; 436/501; 436/506; 436/513; 436/518; 436/528; 436/164; 436/169; 436/172

(58) Field of Classification Search .................. 435/7.1, 435/7.21, 7.92, 7.95, 960, 970, 975, 7.93; 436/501, 506, 513, 518, 528, 164, 169, 172; 422/57, 58, 61, 425
See application file for complete search history.

(56) References Cited

U.S. PATENT DOCUMENTS

| | | | |
|---|---|---|---|
| 7,745,139 B1 | 6/2010 | Wallukat et al. | |
| 2003/0078190 A1 | 4/2003 | Weinberg | |
| 2004/0192634 A1 | 9/2004 | Schulze-Forster et al. | |
| 2006/0135422 A1 | 6/2006 | Moskowitz | |
| 2006/0263835 A1* | 11/2006 | Wallukat | 435/7.92 |

FOREIGN PATENT DOCUMENTS

| | | | |
|---|---|---|---|
| CA | 2363999 | | 6/2000 |
| DE | 199 54 305 A1 * | | 6/2000 |
| WO | WO 0037075 | | 6/2000 |
| WO | 00/39154 | * | 7/2000 |
| WO | 02/10753 | * | 2/2002 |
| WO | WO 02093171 | | 11/2002 |
| WO | WO 2008015218 | | 5/2008 |

OTHER PUBLICATIONS

Wallukat et al., 1999. Patients with preeclampsia develop agonistic autoantibodies against the angiotensin AT1 receptor. Journal of Clinical Investigation 103(7): 945-952.*
Fu et al., 2000. Autoantibodies against the angiotensin receptor (AT1) in patients with hypertension. Journal of Hypertension 18: 945-953.*
Dechend et al., 2000. AT1 receptor agonistic antibodies from preeclamptic patients cause vascular cells to express tissue factor. Circulation 101: 2382-2387.*
Bachy et al., 1976. Hypertension after renal transplantation. British Medical Journal 2: 1287-1289.*
Inigo et al., 2001. Effects of losartan and amlodipine on intrarenal hemodynamics and TGF-beta1 plasma levels in a crossover trial in renal transplant recipients. Journal of the American Society of Nephrology 12: 822-827.*
Dragun et al., "Angiotensin II Type 1-Receptor Activating Antibodies in Renal-Allograft Rejection," N. Engl. J. Med., 352, 6, Feb. 10, 2005, pp. 558-569.
Pitotti et al., "HPLC method for evaluation of urinary angiotensin-converting enzyme: some examples of normal subjects and patients with renal transplantation", Journal of Pharmaceutical and Biomedical Analysis, vol. 4, No. 5, 677-683, 1986.
Colonna et al., "Non-Renin Dependent Hypertension in Renal Allograft Rejections, A structural and functional analysis," Archives of Pathology & Laboratory Medicine, vol. 108, Nr. 2, pp. 117-120, Feb. 1984.
Oldfield et al., "Efferent Neural Projections of Angiotensin Receptor (AT1) Expressing Neurons in the Hypothalamic Paraventricular Nucleus of the Rat" Joural of Neuroedocrinology. vol. 13, No. 2, pp. 139-146, 2001.
Cobankara, et al., "Renin and Angiotensin-Converting Enzyme (ACE) as Active Components of the Local Synovial Renin-Angiotensin System in Rheumatoid Arthritis", Rheumatology International, vol. 25, No. 4, pp. 285-291, May 1, 2005.
Liao, et al., Auto Antibodies Against AT1-Receptor and 1-AdrenergicReceptor in Patients with Hypertension, Hypertension Res., 25, 641-646, 2002.
Walsh, et al., "AT1 Receptor Characteristics of Angiotensin Analogue Binding in Human Synovium", British Journal of Pharmacology, vol. 112, No. 2, pp. 435-442, Jun. 1, 1994.

* cited by examiner

*Primary Examiner* — Gail R Gabel
*Assistant Examiner* — James L Grun
(74) *Attorney, Agent, or Firm* — Fanelli Hoag PLLC

(57) ABSTRACT

The invention relates to a method and an immunological test kit for predicting the risk of transplant rejection by detecting anti-$AT_1$ receptor auto-antibodies in biological materials of a patient to be examined, e.g. by an immune reaction with the $AT_1$ receptor or functionally analogous peptides or proteins thereof. The invention is also directed to the use of the $AT_1$ receptor or functionally analogous peptides or proteins in order to predict (diagnose) the risk of transplant rejection. Said risk exists if anti-$AT_1$ receptor auto-antibodies can be detected in such biological materials, e.g. in body fluids or tissues.

3 Claims, No Drawings

METHOD FOR PREDICTING THE RISK OF TRANSPLANT REJECTION AND IMMUNOLOGICAL TESTKIT

The invention relates to a method and an immunological test kit for predicting the risk of transplant rejection by detecting anti-$AT_1$ receptor auto-antibodies in biological materials of a patient to be examined, e.g. by an immune reaction with the $AT_1$ receptor or functionally analogous peptides or proteins thereof. The invention is also directed to the use of the $AT_1$ receptor or functionally analogous peptides or proteins in order to predict (diagnose) the risk of transplant rejection. Said risk exists if anti-$AT_1$ receptor auto-antibodies can be detected in biological materials, e.g. in body fluids or tissues.

For successful organ transplantation, the donor organ is required to match histologically with the tissue of the recipient as much as possible. Such matching is determined via the HLA system (human leukocyte antigen) which is a complex system of tissue antigens occurring on virtually any cell. Said system plays an important physiological role in immunological defense reactions (recognition of "self" and "non-self"). Prior to each transplantation, therefore, a so-called tissue typing is effected in the organ donor and recipient so as to ensure HLA compatibility as much as possible.

As a result of the immense genetic polymorphism, there is an exceptionally large number of various HLA molecules. Complete match solely is observed in monozygotic twins. Otherwise, HLA molecules are unique to each person.

However, problems exist in that rejection reactions against the transplanted organ cannot be ruled out despite extensive HLA match between recipient and donor.

The object of the invention is therefore to provide an efficient and reliable method allowing positive and rapid predictability as to the risk of a transplant rejection reaction.

The present invention solves this technical problem by providing such a method wherein anti-$AT_1$ receptor auto-antibodies are detected in biological materials of a patient to be diagnosed, a risk of transplant rejection being present or predictable in those cases where these auto-antibodies are detected. According to the invention, it is preferred to detect the auto-antibodies by immune reaction with the $AT_1$ receptor or with peptides or proteins of analogous function. However, it is also possible to detect the auto-antibodies by means of other methods per se known to those skilled in the art, e.g. via electrophoretic separation methods. The invention is based on the surprising evidence that patients exhibiting a transplant rejection reaction with no predictable immunological risk have anti-$AT_1$ receptor auto-antibodies.

It has been possible to demonstrate that there is a relationship between the presence of said auto-antibodies and transplant rejection. In cytobiological and immunohistochemical studies, as well as in investigations on biopsy material, it has been found that there are no additional immunological risk factors to transplant rejection. On the other hand, it has been demonstrated that the presence of the auto-antibodies gives rise to rejection reactions in a recipient with transplanted organs.

In connection with the present invention, a number of general terms will be used as follows:

"Transplant" in the meaning of the invention is an organ or a tissue which has been transplanted or is to be transplanted. In the meaning of the invention, however, transplants can also be particular implants comprised of materials or components incorporated in a body for a limited period of time or for life in order to assume specific substitute functions. For example, such implants can be made of inorganic matter coated with organic substances such as cartilage or bone cells.

According to the invention, "transplant rejection" is understood to be induction of an immune reaction to the transplant in the recipient. An immune reaction in the recipient is a specific protective or defense reaction of the body against the antigens of the transplant.

The "$AT_1$ receptor" according to the invention may be present in its natural cellular environment and can be used together with the material associated with the receptor in its natural state, as well as in isolated form. With respect to its primary, secondary and tertiary structures, the $AT_1$ receptor is well-known to those skilled in the art. Based on the weight of the whole receptor in the preparation to be used according to the invention, the isolated receptor should account for at least 0.5%, preferably at least 5%, more preferably at least 25%, and in a particularly preferred fashion at least 50%. The receptor is preferably used in isolated form, i.e., essentially free of other proteins, lipids, carbohydrates, or other substances naturally associated with the receptor. "Essentially free of" means that the receptor is at least 75%, preferably at least 85%, more preferably at least 95%, and especially preferably at least 99% free of other proteins, lipids, carbohydrates, or other substances naturally associated with the receptor.

In connection with the present invention, the naturally occurring receptor, as well as all modifications, mutants or derivatives of the $AT_1$ receptor can be used. Similarly, an $AT_1$ receptor produced by means of recombinant techniques, which receptor includes amino acid modifications such as inversions, deletions, insertions, additions, etc., can be used according to the invention, provided at least part of the essential function of the $AT_1$ receptor is present, namely, the capability of binding antibodies. The $AT_1$ receptor being used may also comprise exceptional amino acids and/or modifications such as alkylation, oxidation, thiol modification, denaturation, oligomerization and the like. The receptor can also be synthesized by chemical means. According to the invention, the $AT_1$ receptor particularly can be a protein and/or a peptide, or a fusion protein which, in addition to other proteins, peptides or fragments thereof, includes the $AT_1$ receptor as a whole or in part. Using conventional methods, peptides or polypeptides of the $AT_1$ receptor which have functionally analogous properties can be determined by those skilled in the art. For example, such polypeptides or peptides have 50%, 60%, 70%, or 80%, preferably 90%, more preferably 95%, and most preferably 98% homology to peptides identified as $AT_1$ receptor, and said homology can be determined e.g. by means of the Smith-Waterman homology search algorithm, using the MPSRCH program (Oxford Molecular), for example. The term "peptide of an $AT_1$ receptor" used in the present invention comprises molecules differing from their original sequence by deletion(s), insertion(s), substitution(s) and/or other modifications well-known in the prior art or comprising a fragment of the original amino acid molecule, the $AT_1$ receptor still exhibiting the properties mentioned above. Also included are allele variants and modifications. Methods of producing the above changes in the amino acid sequence are well-known to those skilled in the art and have been described in standard textbooks of Molecular Biology, e.g. in Sambrook et al., supra. Those skilled in the art will also be able to determine whether an $AT_1$ receptor thus modified still has the properties mentioned above. Possible $AT_1$ receptor peptides used according to the invention can be e.g. AVHYQSN (SEQ ID NO: 1), SHFYQTR (SEQ ID NO: 2) or GYYFDTN (SEQ ID NO: 3). In the present specification, all of the above-illustrated modifications of the $AT_1$ receptor will be referred to as "functionally analogous peptides or proteins" in brief.

"Biological materials" in the meaning of the invention can be all biological tissues and fluids such as blood, lymph, urine, cerebral fluid. The biological material is collected from the patient and subjected to the diagnosis according to the invention. Obviously, a sample can also be treated or prepared for analysis using specific biochemical and chemical means or methods.

The "auto-antibodies" in the meaning of the invention, which are to be detected, bind the $AT_1$ receptor in a specific fashion. The auto-antibodies can also be modified antibodies (e.g. oligomeric, reduced, oxidized and labelled antibodies). The term auto-antibodies used in the present specification comprises both intact molecules and auto-antibody fragments such as Fab, F(ab')$_2$ and Fv capable of binding specific epitope determinants of the $AT_1$ receptor. In these fragments the auto-antibody's capability of selectively binding its antigen or receptor is retained in part, the fragments being defined as follows:

(1) Fab, the fragment which contains a monovalent antigen-binding fragment of an antibody molecule, can be generated by cleavage of a whole antibody using the enzyme papain, thereby obtaining an intact light chain and part of a heavy chain;

(2) the Fab' fragment of an antibody molecule can be produced by treatment of a whole antibody with pepsin and subsequent reduction, thereby obtaining an intact light chain and part of a heavy chain; two Fab' fragments per antibody molecule are obtained;

(3) F(ab')$_2$, the fragment of the antibody, which can be obtained by treatment of a whole antibody with the enzyme pepsin without subsequent reduction; F(ab')$_2$ is a dimer comprised of two Fab' fragments held together by two disulfide bonds;

(4) Fv, defined as a fragment modified by genetic engineering, which includes the variable region of the light chain and the variable region of the heavy chain and is expressed in the form of two chains; and (5) single-chain antibody (SCA), defined as a molecule modified by genetic engineering, which includes the variable region of the light chain and the variable region of the heavy chain linked by a suitable polypeptide linker to form a genetically fused single-chain molecule.

The term epitope as used in the present invention represents any antigen determinant on the $AT_1$ receptor. Epitope determinants normally consist of chemically active surface groups of molecules such as amino acids or sugar side-chains and normally have specific features of the three-dimensional structure, as well as specific charge properties.

The auto-antibody "binds specifically" to the $AT_1$ receptor, or, in doing so, shows specific immunoreactivity when the auto-antibody assumes its function in a binding reaction in the presence of a heterogeneous population of $AT_1$ receptors or fragments thereof, thereby allowing a conclusion whether the $AT_1$ receptor or another biological structure is present. Under the preset conditions of an immunoassay, the abovementioned auto-antibodies will preferably bind to a specific portion of the $AT_1$ receptor, while no significant binding to other proteins present in the sample will take place.

"Patients" in the meaning of the invention are understood to be all persons, animals, plants, or microorganisms, irrespective of whether or not they exhibit pathological changes. In the meaning of the invention, any biological material collected from cells, tissues, organs, organisms or the like can be biological material of a patient to be diagnosed.

An "immune reaction" in the meaning of the invention is a specific interaction between the $AT_1$ receptor or peptides or proteins of analogous function and auto-antibodies. The immune reaction can be detected using various immunoassays.

"Immunoassays" in the meaning of the invention are assays utilizing the specific interaction between the $AT_1$ receptor and peptides or proteins of analogous function and the auto-antibodies, in order to detect the presence or determine the concentration of the auto-antibodies. For example, the detection and quantification of the auto-antibodies can be performed with the aid of said peptides or proteins of analogous function, e.g. by immunoprecipitation or immunoblotting. For example, immunoassays in the meaning of the invention can be subdivided into the following steps:

1) the auto-antibody/$AT_1$ receptor reaction,
2) if required, separation of the auto-antibody/$AT_1$ receptor complex from other components of the reaction mixture, especially from non-bound auto-antibodies and $AT_1$ receptor, and
3) measuring the response.

As for the auto-antibody/$AT_1$ receptor reaction, various configurations are possible, e.g.
a) precipitation of one reactant with an excess of the other, or
b) competition between known quantities of auto-antibody or $AT_1$ receptor and the material to be investigated.

For example, an assay for auto-antibodies can be performed by
a) using excess $AT_1$ receptors/peptides or proteins of analogous function, or
b) competition between a labelled auto-antibody of known amount and a non-labelled antibody of unknown amount for a defined quantity of $AT_1$ receptor or of peptides or proteins of analogous function.

The $AT_1$ receptor can be immobilized on a solid support to allow separation of the auto-antibody/$AT_1$ receptor complex. For example, the solid support material can be nitrocellulose, polyvinyl chloride or polystyrene, e.g. the well of a microtiter plate. To measure the auto-antibody/$AT_1$ receptor interaction, it is possible to use labelled auto-antibodies, labelled $AT_1$ receptors or secondary reagents, for example. The $AT_1$ receptor can be labelled radioactively or with enzymes or with fluorescent compounds, for example. Irrespective of the label that is used, the response of the auto-antibody/$AT_1$ receptor interaction can be enhanced by utilizing the affinity of the proteins avidin or streptavidin for biotin. The immunoassays used according to the invention can be:

1) immunoassays using a radioactive label:
   a) radioimmunoassays with competitive binding (RIA) and
   b) immunoradiometric assay (IRMA),
2) immunoassays using an enzyme label:
   a) enzyme immunoassays (EIA) and
   b) enzyme-linked immunosorbent assay (ELISA),
3) immunoassays using a combination of radioisotope and enzyme labels (ultrasensitive enzyme radioimmunoassay (USERIA)).

In one embodiment of the invention, detection of human IgA and/or IgG auto-antibodies as auto-antibodies is envisaged. Auto-antibodies are glycoproteins, also referred to as immunoglobulins. Human antibodies can be divided into five classes of immunoglobulins. Class A immunoglobulin (IgA) exists in a form which is dissolved in blood, as well as in a secretory variant. IgA comprises two basic classes. Secretory IgA consists of two immunoglobulin basic molecules, together with a J chain and a secretory component. More specifically, IgA molecules can be prevalent in body secretions. Class IgG immunoglobulins represent the major part among the immunoglobulins. The antibodies of the secondary immune response taking place upon contact of the immune system with a particular antigen largely belong to the IgG class.

To allow a quantitative statement on the $AT_1$ receptor/autoantibody reaction, one of the reactants must be coupled with a detectable label in such a way that the immunological properties of the components are largely retained, e.g. by means of the streptavidin/biotin system or by using secondary antibodies.

In another preferred embodiment of the invention, an immunoprecipitation, a radioimmunoassay, an enzymatic assay, a fluorescent immunoassay, a chemiluminescent immunoassay, a competitive binding assay, an ELISA, and/or a homogeneous immunoassay can be employed as immunoassay, preferably an ELISA. In immunoprecipitation, the reaction between the auto-antibody and the $AT_1$ receptor can be observed in vitro, directly at the point of equilibrium where the concentrations of both components coincide. At this point, an immunoprecipitation takes place. The immunoprecipitation can be performed in semi-solid media such as agar gel. The diffusion of the immunochemical components through such a gel generates a concentration gradient which ensures that the conditions for immunoprecipitation are satisfied at a particular point, provided the immune complexes will form. The position and nature of the immunoprecipitate in the gel furnishes information on the concentrations of the immune components. A qualitative evidence of an immune complex reaction can be obtained by double immunodiffusion. In the simplest form of immunoprecipitation, a thin agarose gel is provided with two small wells receiving a small amount of $AT_1$ receptor and the biological material containing the auto-antibodies. Following 24 hours of diffusion, the formation of immune complexes can be detected by a white line of precipitate between the two wells. A more complex version is the Ochterlony assay wherein the wells are arranged in the form of a circle on the gel plate, with an additional well in the center of the circle. Various dilutions of biological material containing the auto-antibodies are placed in the outer wells, and the solution including the $AT_1$ receptor/peptides or proteins of analogous function is placed in the center of the circle.

Quantitative analysis is possible by simple immunodiffusion. While one component is distributed homogeneously in the gel, the other is allowed to diffuse out of a well. For example, a solution including the $AT_1$ receptor/peptides of analogous function can be mixed into the gel, and a sample of biological material can be placed in the well, which material is to be investigated for an included auto-antibody by formation of a ring of precipitate.

Another possible assay to determine auto-antibodies is the radioimmunoassay (RIA). The RIA is a sensitive immunoassay based on competitive binding of an antigen to an antibody, wherein the amount being bound is determined quantitatively with the aid of radioactively labelled antigens. Advantageously, the RIA allows determination of amounts of substances down to the picogram region.

Another assay for the determination of auto-antibodies is the enzyme immunoassay. This immunoassay is based on enzyme-labelling one reactant, e.g. the secondary antibody. Solid-phase systems such as vessels or pellets coated with antibody or antigen are advantageous, because removal thereof will not give rise to denaturation of proteins. Quantification of bound or free phase is effected by measuring the enzyme activity. For example, a colorless substrate can be added which, when converted by an enzyme, yields a colored product which can be detected by spectroscopy and quantified using a standard sample. As a rule, the substrate solution is added subsequent to separating bound and free phases and, following a predetermined period of time, the reaction is quenched and the optical density of the product is determined, furnishing a measure for the amount of auto-antibodies present in the sample. The sensitivity of the enzyme reaction can be increased in various ways. One method is the principle of enzymatic amplification wherein the product of the first enzymatic reaction generates a closed cycle in a second enzyme system, resulting in a higher amount of colored final product. One example of a closed enzymatic cycle is represented by the enzyme alkaline phosphatase which hydrolyzes $NADP^+$ to $NAD^+$, the latter entering an enzymatic cycle to form large amounts of a colored product of nitrotetrazolium. Other enzymes can be peroxidase or β-galactosidase. For example, luminol, β-galactosidase and p-nitrophenyl phosphate are used as substrates. For example, detection of the bound auto-antibodies can be effected in a second incubation step using a labelled anti-auto-antibody. In a homogeneous immunoassay, the immunocomplexes having formed are not removed.

Another way of detecting the auto-antibodies is by using a fluorescent immunoassay, with fluorescent labels constituting the basis of this assay. For example, the formation of immunocomplexes can be quantified via the label of $AT_1$ receptor/functionally analogous peptides of the bound or free fraction in the immunochemical reaction mixture. For example, fluorescein or rhodamine can be used as fluorescence carriers, or labels based on chelate complexes of rare earths, such as organometallic coordination complexes of europium.

Furthermore, the auto-antibodies can be detected in a chemiluminescent immunoassay which, advantageously, is a simple and stable test system. Chemiluminescence is observed when a high-energy chemical reaction produces molecules wherein the electrons are in an excited state. Photons are emitted when these excited molecules return to their ground state. For example, such chemiluminescent molecules can be coupled to $AT_1$ receptors or peptides of analogous function and used in an immunoassay. For example, the $AT_1$ receptors/functionally analogous peptides can be labelled with luminol or acridinium salts. Acridinium salts undergo chemiluminescent reactions without requiring a catalyst, as is the case with luminol derivatives. The catalysts comprise a wide spectrum of substances ranging from simple transition metal cations up to complex enzymes. Advantageously, acridinium salts merely require addition of a dilute alkaline hydrogen peroxide solution to trigger a chemiluminescent reaction.

It is also possible to detect the auto-antibodies in a competitive binding assay wherein limited amounts of labelled $AT_1$ receptor or functionally analogous peptide competing for the auto-antibody are employed. Such a method can be advantageous in those cases where purified $AT_1$ receptors or functionally analogous peptides are available for labelling. For example, an $AT_1$ receptor bound to a solid phase can be supplied, to which receptor an auto-antibody present in the sample can bind.

The invention also relates to the use of the anti $AT_1$ receptor or of functionally analogous peptides or proteins in order to predict the risk of transplant rejection. To this end, the autoantibodies are detected in the above-described immunoassays in a per se known manner.

The invention also relates to an immunological test kit including the $AT_1$ receptor or peptides or proteins of analogous function. The test kit of the invention comprises at least one complete $AT_1$ receptor or functionally analogous peptides or proteins of said receptor, optionally bound to a solid phase. Furthermore, the test kit may also comprise buffers, a specific conjugate together with an enzyme, a wash solution, a substrate solution to detect the immune reaction, and/or a quenching solution. Using these substances, a person skilled in the art will be able to perform e.g. an ELISA to detect the auto-antibodies. The buffers, specific conjugate plus enzyme, wash solution, substrate solution to detect the immune reaction, and quenching solution are well-known to those skilled in the art. For example, it would be sufficient to have the test kit comprise a freeze-dried $AT_1$ receptor or peptides or proteins of $AT_1$-analogous function and to add the buffers and other solutions immediately prior to testing the biological material. However, it is also possible to provide the test kit with the $AT_1$ receptor or its functionally analogous peptides or proteins bound to a solid phase. To detect the auto-antibodies, the specific conjugate, wash solution, substrate solution, and quenching solution, which can be components of the test kit, have to be added according to a mode well-known to those skilled in the art.

In another advantageous embodiment of the invention, it is envisaged that the test kit is a test strip comprising the $AT_1$ receptor or its functionally analogous peptides or proteins immobilized on a solid phase. For example, the test strip can be immersed in serum or other biological samples and incubated. Using a specific biochemical reaction on the test strip after formation of the $AT_1$ receptor/auto-antibody complex, a specific color reaction can be triggered, by means of which the auto-antibodies can be detected.

The test system of the invention permits quantification of anti-$AT_1$ receptor/auto-antibodies directly in a biological material, e.g. in plasma of patients. The detection method according to the invention is timesaving and cost-effective. Large amounts of samples can be tested and, owing to the low amount of equipment required, routine laboratories can be used.

Without intending to be limiting, the invention will be illustrated with reference to the following example.

EXAMPLE $AT_1$ ELISA

A suitable streptavidin-coated microtiter plate is loaded with the biotinylated peptide SAFHYESQNSTL (SEQ ID NO: 4). To this end, 100 µl of a solution per well on the microtiter plate is incubated with 5 µg/ml in a suitable dilution buffer. To measure the non-specific binding, wells are also filled with 100 µl of dilution buffer only.

Subsequent to the time period of reaction, the peptide solution is removed by decanting, and each well is washed three times with about 250 µl of a suitable wash buffer.

Thereafter, 100 µl/well of sera diluted in dilution buffer are placed on both the peptide-loaded and comparative plates and incubated. Subsequently, the wells are washed as described above.

The bound antibodies are detected using a goat-anti-human immunoglobulin G antibody having peroxidase coupled thereto. To this end, the antibody is diluted in dilution buffer and incubated (100 µl/well), and this is followed by three wash steps (see above).

Following addition of 100 µl of a ready-for-use substrate solution (e.g. 3,3',5,5'-tetramethylbenzidine), a color develops depending on the amount of peroxidase in the well. The substrate reaction is terminated by addition of 100 µl of 0.5 M sulfuric acid. The absorption is measured at 450 nm.

For evaluation, the difference between the absorptions of peptide-loaded microtiter plate and comparative plate with no peptide is formed. Samples having higher absorption than the cut-off are positive. The cut-off is calculated from the mean value of the absorption of negative donors plus three times the standard deviation. In general, a cut-off control or a standard dilution series allowing quantification in relative units is co-performed in the test.

The invention claimed is:

1. A method of detecting auto-antibodies capable of binding to the peptide SAFHYESQNSTL (SEQ ID NO:4) in a blood or serum sample comprising:
   (a) obtaining the blood or serum sample from a patient at risk of rejecting a transplanted organ having an extensive HLA match with said patient;
   (b) contacting said blood or serum sample with the peptide to obtain a peptide-antibody complex; and
   (c) detecting said auto-antibody by detecting said peptide-antibody complex,
   wherein the peptide is immobilized on a solid support.

2. The method of claim 1 wherein the support is washed following step (b).

3. The method of claim 1 wherein the steps (b) and (c) are carried out with an immunoassay selected from the group consisting of a radioimmunoassay, an enzyme immunoassay, a fluorescent immunoassay, a chemiluminescent immunoassay, a competitive binding assay, an ELISA, and a homogeneous immunoassay.

* * * * *

SEQUENCE LISTING

```
<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Val His Tyr Gln Ser Asn
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser His Phe Tyr Gln Thr Arg
1               5

<210> SEQ ID NO 3
```

-continued

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Tyr Phe Asp Thr Asn
  1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ala Phe His Tyr Glu Ser Gln Asn Ser Thr Leu
  1               5                  10
```